United States Patent
Gomez et al.

(10) Patent No.: US 12,274,728 B2
(45) Date of Patent: Apr. 15, 2025

(54) **PREPARATION COMPRISING OMEGA-3 FATTY ACID SALTS AND EXTRACTS OF GUM RESINS FROM *BOSWELLIA* SPECIES**

(71) Applicant: Evonik Operations GmbH, Essen (DE)

(72) Inventors: Mario Gomez, Darmstadt (DE); Bodo Speckmann, Kahl (DE); Michael Schwarm, Alzenau (DE); Oliver Werz, Jena (DE)

(73) Assignee: Evonik Operations GmbH, Essen (DE)

( * ) Notice: Subject to any disclaimer, the term of this patent is extended or adjusted under 35 U.S.C. 154(b) by 595 days.

(21) Appl. No.: 17/631,320

(22) PCT Filed: Jul. 30, 2020

(86) PCT No.: PCT/EP2020/071556
§ 371 (c)(1),
(2) Date: Jan. 28, 2022

(87) PCT Pub. No.: WO2021/019037
PCT Pub. Date: Feb. 4, 2021

(65) Prior Publication Data
US 2022/0265749 A1 Aug. 25, 2022

(30) Foreign Application Priority Data
Aug. 1, 2019 (EP) .................................. 19189564

(51) Int. Cl.
| | | |
|---|---|---|
| *A61K 36/324* | (2006.01) | |
| *A23K 10/30* | (2016.01) | |
| *A23K 20/105* | (2016.01) | |
| *A23K 20/142* | (2016.01) | |
| *A23K 20/158* | (2016.01) | |
| *A23K 20/163* | (2016.01) | |
| *A23L 33/00* | (2016.01) | |
| *A23L 33/105* | (2016.01) | |
| *A23L 33/12* | (2016.01) | |
| *A23L 33/175* | (2016.01) | |
| *A61K 31/202* | (2006.01) | |
| *A61K 47/12* | (2006.01) | |
| *A61K 47/14* | (2017.01) | |
| *A61K 47/36* | (2006.01) | |

(52) U.S. Cl.
CPC ............ *A61K 36/324* (2013.01); *A23K 10/30* (2016.05); *A23K 20/105* (2016.05); *A23K 20/142* (2016.05); *A23K 20/158* (2016.05); *A23K 20/163* (2016.05); *A23L 33/105* (2016.08); *A23L 33/12* (2016.08); *A23L 33/175* (2016.08); *A23L 33/40* (2016.08); *A61K 31/202* (2013.01); *A61K 47/12* (2013.01); *A61K 47/14* (2013.01); *A61K 47/36* (2013.01); *A23V 2002/00* (2013.01); *A61K 2236/331* (2013.01); *A61K 2236/37* (2013.01); *A61K 2236/53* (2013.01)

(58) Field of Classification Search
None
See application file for complete search history.

(56) References Cited

U.S. PATENT DOCUMENTS

| | | |
|---|---|---|
| 2006/0246115 A1 | 11/2006 | Rueda et al. |
| 2011/0262552 A1 | 10/2011 | Chamberland et al. |
| 2013/0052271 A1 | 2/2013 | Sternasty |
| 2015/0126602 A1 | 5/2015 | Bannenberg et al. |
| 2017/0360072 A1 | 12/2017 | Knaup et al. |
| 2018/0271818 A1 | 9/2018 | Bannenberg et al. |
| 2019/0201363 A1 | 7/2019 | Bannenberg et al. |
| 2020/0281883 A1 | 9/2020 | Bannenberg et al. |

FOREIGN PATENT DOCUMENTS

| | | |
|---|---|---|
| JP | 2008-531731 A | 8/2008 |
| JP | 2018-502085 A | 1/2018 |
| WO | WO 2006/096579 A1 | 9/2006 |
| WO | WO 2010/037213 A1 | 4/2010 |
| WO | WO 2013/170006 A2 | 11/2013 |
| WO | WO 2016/102323 A1 | 6/2016 |

OTHER PUBLICATIONS

Ulbrich et. al. (Targeted Drug Delivery with Polymers and Magnetic Nanoparticles: Covalent and Noncovalent Approaches, Release Control, and Clinical Studies, Chemical Reviews, American Chemical Society, 2016, 116, 5338-5431). (Year: 2016).*
International Search Report and Written Opinion issued Oct. 26, 2020 in PCT/EP2020/071556 filed Jul. 30, 2020, 14 pages.
European Search Report issued Feb. 6, 2020 in European Application 19189564.8, 9 pages.

* cited by examiner

Primary Examiner — Aaron J Kosar
Assistant Examiner — Jacob A Boeckelman
(74) Attorney, Agent, or Firm — Oblon, McClelland, Maier & Neustadt, L.L.P.

(57) ABSTRACT

Preparations may include at least one extract of gum resins from *Boswellia* species and at least one omega-3 fatty acid salt selected from eicosapentaenoic acid (EPA) and docosahexaenoic acid (DHA). Surprisingly, such combinations of extracts of gum resins from *Boswellia* species and polyunsaturated fatty acid salt can cause a marked and unexpected increase in the biosynthesis of specialized pro-resolving mediators (SPM) in a synergistic manner, proposing benefit for resolution of inflammatory conditions.

23 Claims, 6 Drawing Sheets

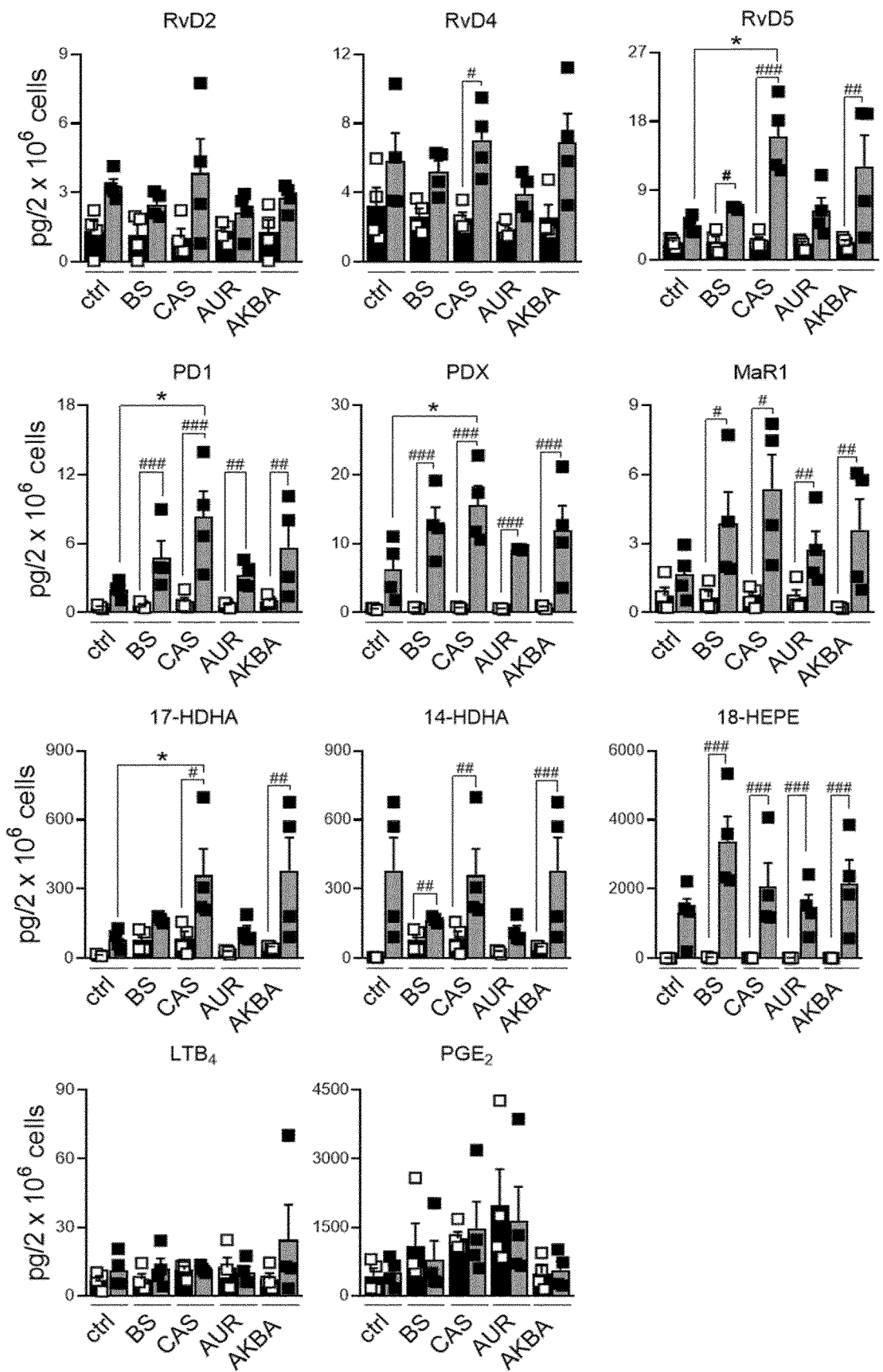
Fig.1: Boswellia extracts stimulate LM biosynthesis formation in human M1-like macrophages.

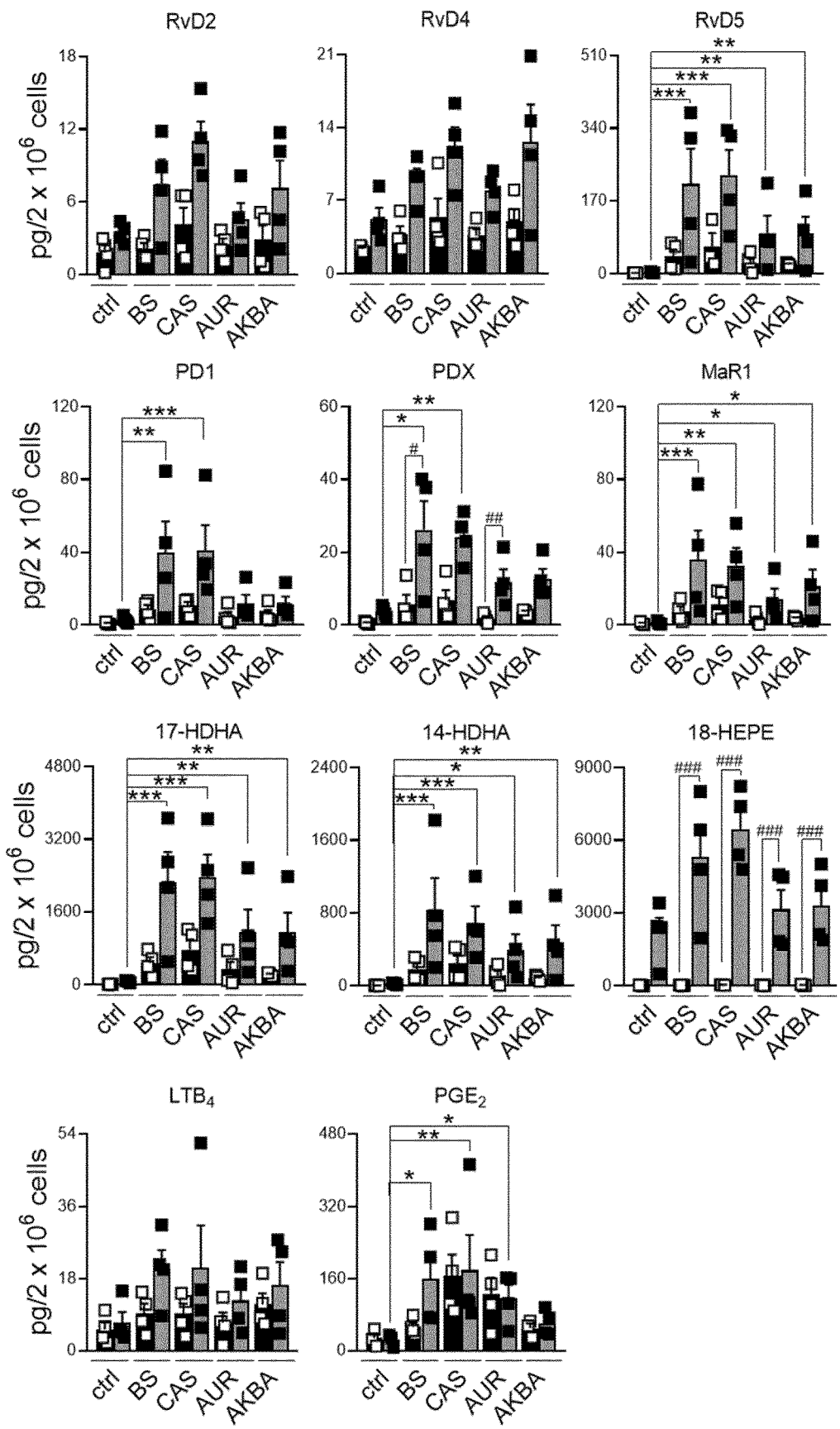
Fig. 2: Boswellia extracts stimulate LM biosynthesis formation in human M2-like macrophages.

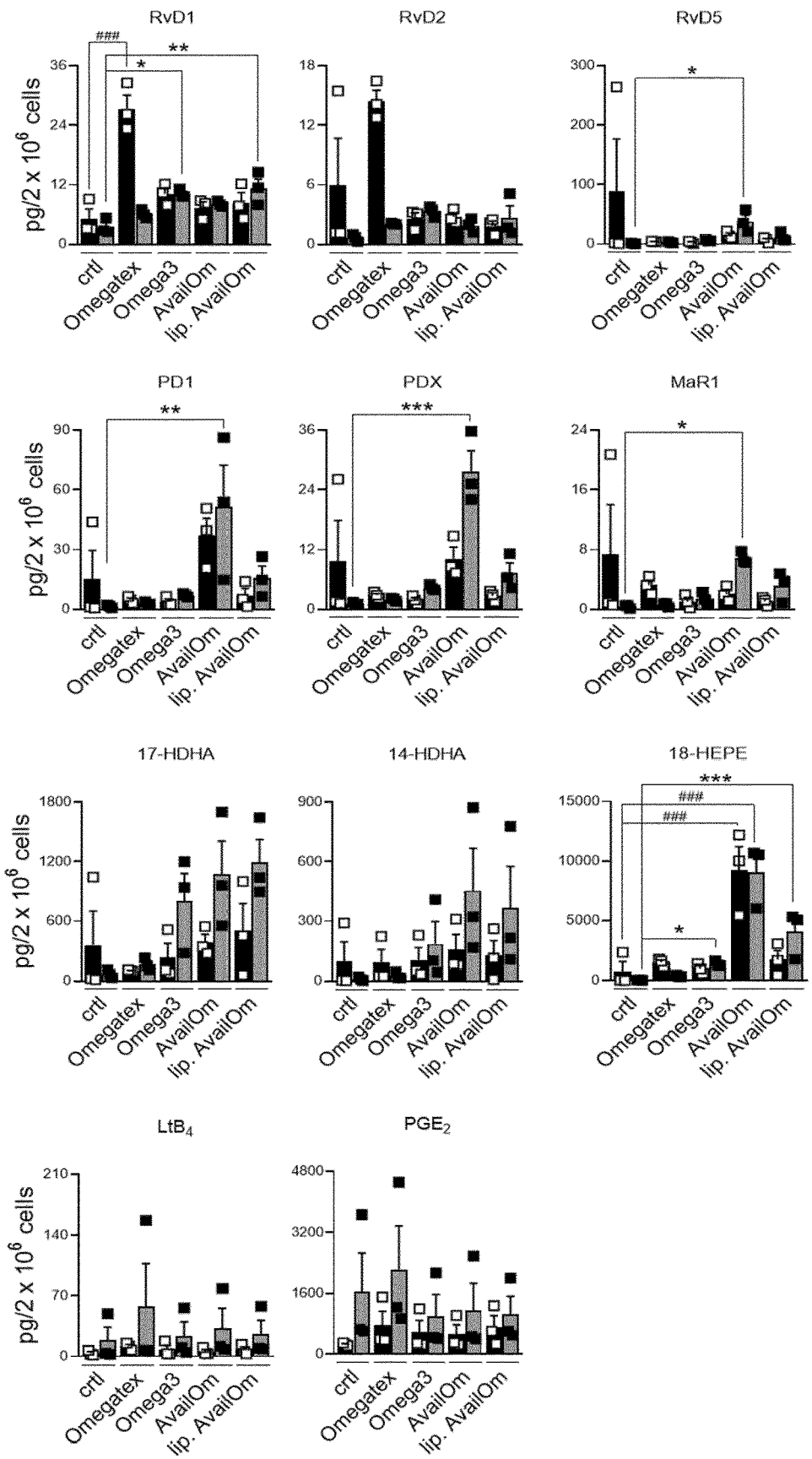
Fig. 3: Stimulation of LM biosynthesis formation in human M1 macrophages

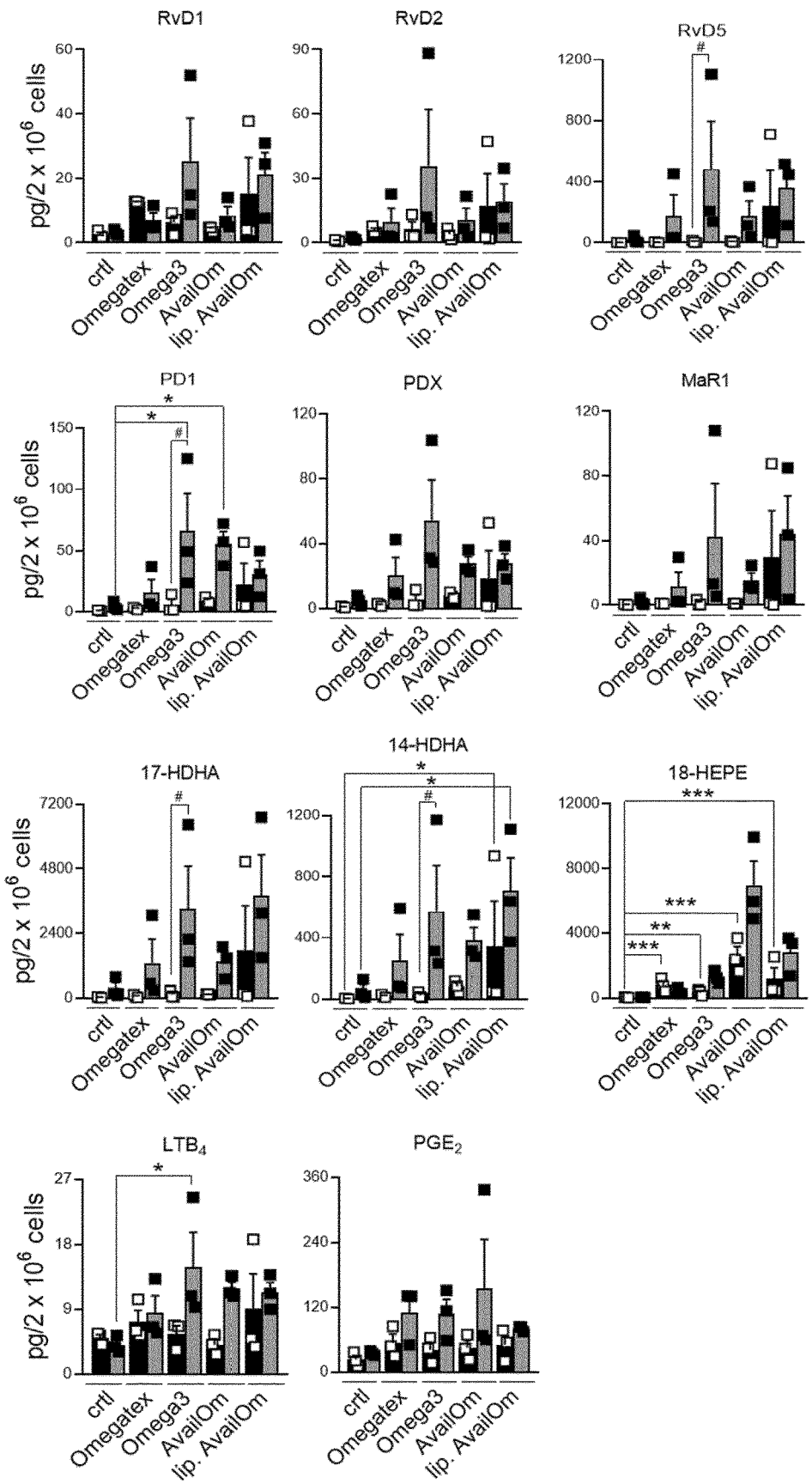
Fig. 4: Stimulation of LM biosynthesis formation in human M2 macrophages

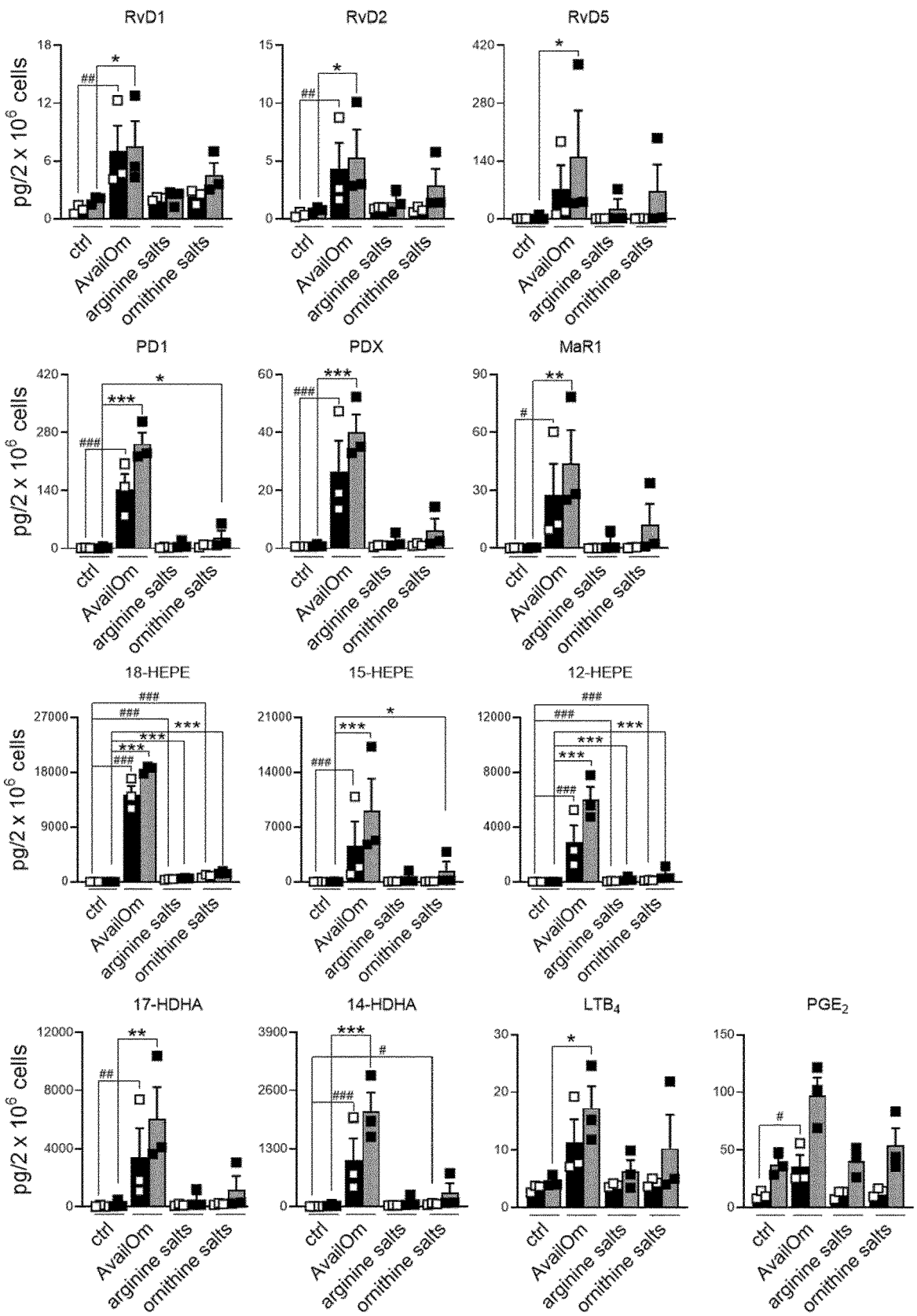
Fig. 5: Stimulation of LM biosynthesis formation in human M2 macrophages for omega-3 lysine (AvailOm®), arginine and ornithine salts

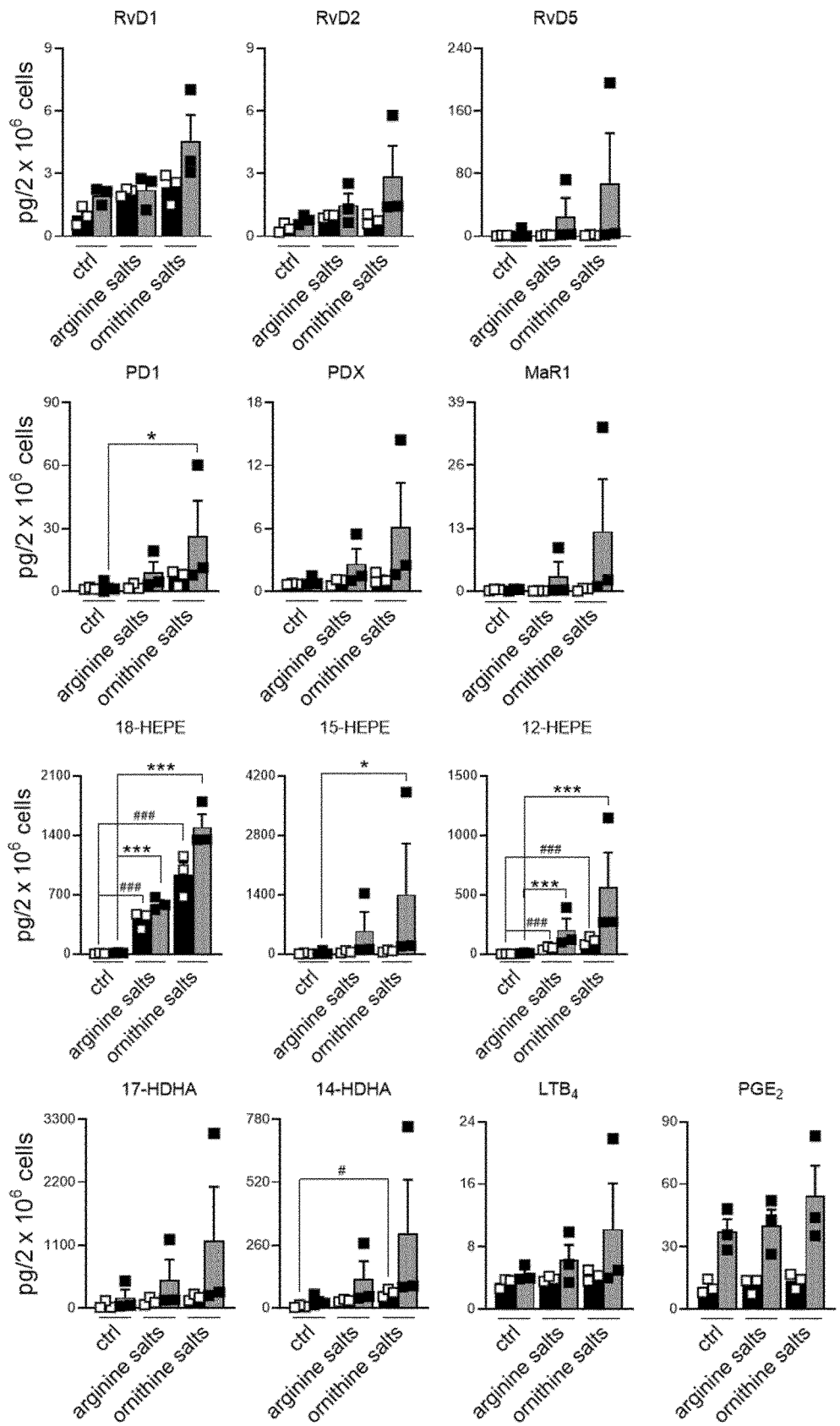
Fig. 6: Stimulation of LM biosynthesis formation in human M2 macrophages for omega-3 arginine and ornithine salts

PREPARATION COMPRISING OMEGA-3 FATTY ACID SALTS AND EXTRACTS OF GUM RESINS FROM *BOSWELLIA* SPECIES

CROSS-REFERENCE TO RELATED APPLICATIONS

The present application is the national stage of international application PCT/EP2020/071556, filed on Jul. 30, 2020, and claims the benefit of the filing date of European Appl. No. 19 189 564.8, filed on Aug. 1, 2019.

The current invention concerns a preparation comprising at least one omega-3 fatty acid salt, comprising at least one omega-3 fatty acid selected from eicosapentaenoic acid (EPA) and docosahexaenoic acid (DHA), in combination with extracts of gum resins from *Boswellia* species and their use to stimulate the production of specialized pro-resolving lipid mediators (SPMs) for actively resolution of inflammation.

Dietary intake of omega-3 fatty acids, namely alpha-linoleic acid (ALA), EPA and DHA, is beneficial for human health, in particular with respect to e.g. the amelioration of rheumatoid arthritis and reduction of cardiovascular disease risk factors [1, 2]. Various seafood products are a source of dietary EPA/DHA, but their consumption is often not sufficient to meet the recommended dietary allowance (typically 500 mg EPA and DHA per day) [3]. This gap is closed by the widespread use of dietary supplements or fortified foods containing omega-3 fatty acids [4]. Dietary supplements are concentrated sources of nutrients or other substances with a nutritional or physiological effect, whose purpose is to supplement the normal diet (www.efsa.europa.eu/en/topics/topic/food-supplements). For example, omega-3 fatty acid supplements often contain either triglycerides or omega-3 ethyl esters of EPA/DHA from fish oil, krill oil, or algae.

Omega-3 fatty acids in general have anti-inflammatory, cardio- and neuroprotective effects [2, 5]. Their modes of action involve e.g. direct scavenging of reactive oxygen species, alteration of cell membrane fluidity, which subsequently affects cellular signaling events, modulation of the activity of transcription factors such as PPARγ and NFkappaB that orchestrate the biosynthesis of pro- and anti-inflammatory cytokines, and competitive exclusion of substrates that are converted to proinflammatory mediators by cyclooxygenases and lipoxygenases.

Since daily consumption of these omega-3 sources with food or nutritional supplements is limited, it's important to assure maximum bioavailability of these fatty acids. Bioavailability of hydrophobic nutrients in the digestive system is often low and represents a challenge especially for supplements, because they are frequently consumed independently from a meal in the form of capsules or pills. Secretion of digestive fluids (bile acids, phospholipids, lipases) is hardly or not at all induced in the fasted state, which results in incomplete enzymatic hydrolysis of fats and oils, low solubilization and bioavailability.

Additional bioavailability challenges arise, when advanced formulation technologies are used to skip parts of the digestive systems in order to release omega-3 fatty acids in the lower part of the digestive system, e.g. in the small or large intestine. Capsules or tablets coated with respective release polymers can be used for this purpose. In these systems, the above mentioned, natural solubilization mechanisms are less effective, which reduces bioavailability and has to be compensated by appropriate measures.

The same is true for the supply of omega-3 fatty acids to isolated cells and tissues for in vitro cultivation, e.g. as part of serum-free cell culture medium compositions. In those applications, solubilization in the digestive tract is preferably mimicked by formulations that are close to the natural system to maximize biocompatibility and bioavailability. For the addition to cell culture media, it is also essential that the fatty acids are dispersed in the medium in a way that allows optimum passage through sterile filters.

Various approaches have been developed to solve the bioavailability problem, either by formulation, chemical modification of omega-3 fatty acids or both. One promising approach is the hydrolysis and subsequent saponification of omega-3 fatty acid esters, which mimics part of the natural digestive process and thereby increases solubility. WO2016102323A1 describes compositions comprising polyunsaturated omega-3 fatty acid salts that can be stabilized against oxidation.

Lipid mediators (LM) play important roles in promoting as well as in resolving inflammation, and therefore regulate various inflammatory disorders and inflammation-related diseases. Among the pro-inflammatory LM, the cyclooxygenase (COX)-derived prostaglandins such as $PGE_2$ and 5-lipoxygenase (LOX)-derived products such as $LTB_4$ are of particular interest. These inflammation-promoting eicosanoids are formed from arachidonic acid (AA, 20:4).

On the other hand, LOX enzymes and to some degree also COX may act in conjunction and convert AA to anti-inflammatory lipoxins or they may metabolize eicosapentaenoic acid (EPA, 20:5) and docosahexaenoic acid (DHA, 22:6) to inflammation-resolving LM (so-called "specialized pro-resolving mediators"=SPM). More recently, several oxygenation products of omega-3 and omega-6 fatty acids have been identified and functionally characterized as crucial mediators of their beneficial health effects, in particular with respect to the amelioration of chronic inflammatory conditions [6]. These SPM include maresins (MaR), E- and D-series resolvins (RvE and RvD), protectins, lipoxins, and precursors thereof such as 18-hydroxy-eicosapentaenoic acid (18-HEPE) and 17,18-epoxyeicosatetraenoic acid (17, 18-EEQ). SPM are endogenously formed by LOX, COX-2, and cytochrome P450 monooxygenases (CYP450), and act as potent agonists of active inflammation resolution, signaling via G-protein coupled receptors at nanomolar concentrations.

The effectiveness of SPM against a multitude of infectious and inflammatory diseases has been demonstrated in studies with rodents [6]. For example, RvE1, RvD2, protectin D1 (PD1), and $LXA_4$ enhance the clearance of pathogenic *Pseudomonas gingivalis* [7], *E. coli* [8], Herpes simples [9], *Candida* [10], H5N1 Influenza [11].

$LXA_4$, $LXB_4$, RvE1, RvE3, RvD1-6, PD1, MaR1, MaR2 are protective in models of periodontitis, cystic fibrosis, neuroinflammation, ischemic stroke, Alzheimer's disease [12], atherosclerosis [13], non-alcoholic fatty liver disease [14], corneal injury [15], retinopathy [16], glaucoma [17], colitis [18], asthma [19, 20], insulin resistance [14], arthritis [21], and pain [22]. Moreover, several precursors of SPM have themselves been shown to exert pro-resolving effects. For example, 18-hydroxy-eicosapentaenoic acid (18-HEPE) counteracts the development of cardiovascular diseases by inhibiting monocyte adhesion to vascular endothelial cells [23] and by inhibiting pressure overload-induced maladaptive cardiac remodeling [24]. Similarly, 17,18-EEQ has cardio-protective, anti-arrhythmic, vasodilatory, and anti-inflammatory properties [5]. Paracrine secretion of ARAderived 15-HETE by enteric glial cells supports gut barrier function, a process that is impaired in e.g. Crohn's disease [25].

Translation of these promising preclinical findings towards improving human health has however shown to be challenging. Direct delivery of SPM by intravenous or intraperitoneal injection, as has been done in experimental studies, is not feasible for humans, particularly not in the context of preventive approaches. Oral delivery of SPM-containing supplements or foods is not reasonable because of the relatively short half-life of SPM in biological fluids, which are therefore unlikely to reach their target tissue. Clinical trials with the SPM precursors EPA/DHA have yielded inconclusive or null results, especially for patients with inflammatory bowel diseases, asthma, and traits of the metabolic syndrome [2]. This lack of benefit for humans contrasts with the effective treatment of the respective animal disease models by SPM [6]. We reason that the endogenous conversion of omega-3 (and omega-6) to SPM is a crucial step which is decisive for delivering successful outcomes from any interventions aiming to prevent, cure, or treat inflammatory diseases with polyunsaturated fatty acids (PUFA). We also conceive that the SPM-producing machinery is dysfunctional under certain conditions. This idea is supported by findings of reduced (local or circulating) SPM levels in diabetic wounds [26], metabolic syndrome [27], asthma [19, 28], ulcerative colitis [29], Crohn's disease [25], and periodontitis [30], as well as reduced expression or activity of SPM-producing enzymes in severe asthma [28], ulcerative colitis [29], cystic fibrosis [31], periodontitis [30], and Alzheimer's disease [12].

Two major aspects, which determine the degree of LM formation in the cells are the amount and activity of biosynthetic enzymes (COX, LOX, CYPs), which can be influenced by *Boswellia* extracts and the amount of substrate (AA, EPA and DHA) available.

The objective of this invention is therefore to provide a technology that promotes endogenous SPM formation inside an organism to provide a benefit to humans and animals suffering from the above-mentioned conditions and that are in need of novel strategies to prevent, ameliorate or cure such and similar conditions, where supplementation of omega-3s alone has yielded little or no success.

This goal is achieved by the invention providing mixtures of omega-3 fatty acids and/or theirs salts with extracts of gum resins from *Boswellia* species and their use to stimulate the production of specialized pro-resolving lipid mediators (SPMs) for actively resolving inflammation.

It was found that supplementation with omega-3 fatty acid salts, comprising at least one polyunsaturated fatty acid salt comprising at least one omega-3 fatty acid selected from eicosapentaenoic acid (EPA) and docosahexaenoic acid (DHA) and at least one basic amino acid combined with extracts of gum resins from *Boswellia* species surprisingly improve the formation of specialized pro-resolving mediators and their precursors in a synergistic manner.

*Boswellia*, also known as Indian frankincense, is an herbal extract taken from the gum resin of *Boswellia* trees. The resin made from *Boswellia* bark has been used for centuries in Asian and African folk medicine. It's believed to display a benefit in the treatment of chronic inflammatory illnesses as well as a number of other health conditions. *Boswellia* preparation are available as a resin, pill, or cream. Extracts of gum resins from *Boswellia* species (*Boswellia* extracts) have demonstrated to be effective in reducing inflammation and can be useful in treating numerous conditions such as osteoarthritis, rheumatoid arthritis, asthma, inflammatory bowel disease.

Because *Boswellia* extract is an effective anti-inflammatory, it can be an effective painkiller and may prevent the loss of cartilage.

A variety of tetra- and pentacyclic triterpene acids in *Boswellia* extracts contribute to the anti-inflammatory properties, such as boswellic acids, tirucallic acids, roburic acids, lupeolic acids, and nyctanthic acid. In particular, boswellic acids are bioactive and include β-boswellic acid, acetyl-β-boswellic acid, 11-keto-β-boswellic acid (KBA), and acetyl-11-keto-β-boswellic acid (AKBA). Boswellic acids are a series of pentacyclic triterpene molecules that are produced by plants in the genus *Boswellia*. Like many other terpenes, boswellic acids appear in the resin of the plant that exudes them; it is estimated that they make up 30% of ethanolic extracts produced from resin of *Boswellia serrata*. KBA and AKBA inhibit 5-lipoxygenase (5-LOX), an enzyme that produces leukotrienes. AKBA is thought to be the most powerful of the four boswellic acids to inhibit 5-LOX. However, other research suggests other boswellic acids and triterpene acids that are responsible for the anti-inflammatory properties of the extracts by inhibition of cathepsin G, LL-37, microsomal prostaglandin E2 synthase (mPGES)-1 and IkappaB kinase.

A preparation of omega-3 fatty acids eicosapentaenoic acid (EPA), docosahexaenoic acid (DHA), combined with *Boswellia* extracts can be applied, for example, as a dietary supplement or orally administered drug with a suitable coating to be released in defined regions of the gastrointestinal tract. Additionally, such compositions formulated on a carrier systems (e.g. nanocellulose) can also be topically used for resolving inflammatory disorders of the skin.

The omega-3 forms that are commonly used in food fortification or nutritional supplements are krill oil, fish oil, or ethyl esters derived from the former. Recently, a technology has been described to stabilize EPA/DHA free fatty acids with amino acids resulting in solid and somewhat inert salts of EPA/DHA that can be introduced into e.g. food or supplement preparations. WO2016102323A1 describes compositions comprising polyunsaturated omega-3 fatty acid salts that can be stabilized against oxidation. WO2017202935A1 discloses a method for preparing a composition comprising omega-3 fatty acid salts and amines wherein a paste comprising one or more omega-3 fatty acid(s), one or more basic amine(s) and 20% by weight or less water, based on the total weight of the paste, is kneaded until a homogenous paste is obtained.

Therefore, the current invention of a boosting technology for intracellular SPM production paves the way for novel opportunities in the prevention and treatment of various inflammatory conditions such as diseases, in particular cardiovascular, joints & chronic inflammatory diseases.

The present invention is directed to a preparation comprising at least one extract of gum resins from *Boswellia* species and at least one polyunsaturated fatty acid salt comprising at least one omega-3 fatty acid selected from eicosapentaenoic acid (EPA) and docosahexaenoic acid (DHA) and at least one basic amino acid.

The extract according to the present invention is prepared from one or more of the following: *Boswellia serrata, Boswellia carterii, Boswellia papyrifera, Boswellia ameero, Boswellia bullata, Boswellia dalzieffi, Boswellia dioscorides, Boswellia elongata, Boswellia frereana, Boswellia nana, Boswellia neglecta, Boswellia ogadensis,*

*Boswellia pirottae, Boswellia popoviana, Boswellia rivae, Boswellia sacra* and *Boswellia socotrana*, preferably *Boswellia serrata*.

The extract is preferably prepared by using hydro-distillation, steam distillation, extraction by percolation, extraction under ultrasonic waves, solvent extraction, Soxhlet's extraction, supercritical fluid extraction or membrane nanofiltration.

In a preferred embodiment of the present invention, the preparation comprises one or more boswellic acids, preferably selected from beta-boswellic acid, acetyl-beta-boswellic acid, 11-keto-beta-boswellic acid and 3-O-acetyl-11-keto-beta-boswellic acid (AKBA), alpha-boswellic acid, 3-O-acetyl-alpha-boswellic acid, and 3-O-acetyl-beta-boswellic acid.

In an alternative embodiment, the preparation further comprises one or more of the following: acid resin, gum, tetra- and pentacyclic triterpene acids, incensole acetate, phellandrene, (+)-cis- and (+)-trans-olibanic acids.

According to the present invention, the fatty acids are selected from the omega-3 fatty acids EPA and DHA.

It is preferred, when the omega-3 fatty acid salts have an organic counter ion selected from lysine, arginine, ornithine, choline and mixtures of the same.

It is particularly preferred to use fatty acid salts comprising EPA and DHA and having an organic counter ion selected from lysine, arginine and ornithine. The lysine salts of EPA and DHA are even more preferred.

In an alternative configuration, the preparation comprises at least 10 weight-% of *Boswellia* extract, preferably at least 20 weight-%, more preferably at least 30 weight-% and most preferably at least 40 weight-% of *Boswellia* extract.

In another configuration, the preparation comprises at least 10 weight-% of polyunsaturated fatty acid salt, preferably at least 20 weight-%, more preferably at least 30 weight-% and most preferably at least 40 weight-% of polyunsaturated fatty acid salt.

It is further preferred, when the preparation comprises at least 40 weight-% of *Boswellia* extract and at least 40 weight-% of polyunsaturated fatty acid salt.

Another preferred configuration of the present invention are formulations of omega-3 dispersions (presumably liposomes) to further improve bioavailability. Such dispersion formulations preferably consist of phospholipid mixtures (e.g. deoiled sunflower lecithin) or defined phospholipids, e.g. dioleylphospatidylcholine (DOPC). Most preferred forms of such dispersion formulations contain free omega-3 fatty acid salts.

Therefore, in a preferred embodiment, the preparation further comprises at least one phospholipid, preferably selected from a deoiled phospholipid with a phosphatidylcholine content of greater than 70 weight-%, preferably greater 90 weight-% and a phosphatidylethanolamine content lower than 5 weight-%, preferably lower than 1 weight-% or a non-hydrogenated phospholipid having an oleic and/or linoleic acid content of greater than 70 weight-% of total fatty acids.

In a further preferred embodiment, the preparation comprises a dispersion of at least one phospholipid and at least one polyunsaturated fatty acid salt. It is particularly preferred to use omega-3 fatty acids.

In a further preferred configuration of the present invention the mass ratio of phospholipid to fatty acid salt is greater than 0.001, preferably greater than 0.05, more preferably greater than 0.01, more preferably greater than 0.09, most preferably greater than 0.39.

In an alternative embodiment the preparation is in the form of a powder or of a liquid that result in colloidal dispersions with mean particle sizes of smaller than 1 μm, preferably smaller than 500 nm, most preferably smaller than 250 nm when mixed with water at a pH value between pH 6.5 and 7.5.

In another embodiment the components are finely dispersed in each other so that both phospholipid and fatty acid salts are present and detectable in amounts of 100 μg and smaller.

In another preferred embodiment, the weight ratio of *Boswellia* extract with relation to the polyunsaturated fatty acid salt is between 0.5:1 to 1:0.5.

Naturally, free fatty acids are absorbed in the small intestine and are therefore not available in the large intestine. A preferred formulation for enteral delivery of a preparation of this invention is a formulation that provides protection against gastric conditions, or a formulation that provides targeted release of the preparation in the small intestine or a formulation that provides targeted release of the preparation in the large intestine.

Another aspect of the invention is therefore the preparation according to the present invention further comprising a targeted-release formulation. A targeted-release formulation according to the present invention is a formulation which ensures the delivery of the omega-3 fatty acids to a specific target in the body. A preferred formulation of such preparations promotes enteral or colonic delivery in the lower small intestine or in the large intestine. The targeted-release formulation can be obtained by adding enteric polymers to the matrix of the dosage form, or by adding a coating to the dosage form, preferably an enteric coating.

An enteric coating is a barrier applied on oral medication that prevents its dissolution or disintegration in the gastric environment. Most enteric coatings work by presenting a surface that is stable at the intensely acidic pH found in the stomach but breaks down rapidly at a higher pH (alkaline pH). For example, they will not dissolve in the gastric acids of the stomach (pH ~3), but they will in the alkaline (pH 7-9) environment present in the small intestine.

Therefore, in an advantageous configuration, the targeted-release formulation comprises a coating, preferably selected from methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein.

As an enteric coating it is preferred to use a polymer polymerized from 10 to 30% by weight methyl methacrylate, 50 to 70% by weight methyl acrylate and 5 to 15% by weight methacrylic acid.

The polymer dispersion as disclosed may preferably comprise 15 to 50% by weight of a polymer polymerized from 20 to 30% by weight methyl methacrylate, 60 to 70% by weight methyl acrylate and 8 to 12% by weight methacrylic acid. Most preferred the polymer is polymerized from 25% by weight methyl methacrylate, 65% by weight methyl acrylate and 10% by weight methacrylic acid.

A 30% by weight aqueous dispersion of a polymer polymerized from 25% by weight methyl methacrylate, 65% by weight methyl acrylate and 10% by weight methacrylic acid corresponds to the commercial product EUDRAGUARD® biotic.

The percentages of the monomers add up to 100%. The functional polymer is applied in amounts of 2-30 mg/cm$^2$, preferably 5-20 mg/cm$^2$.

In a preferred configuration, the preparation further comprises one or more of the following anthocyanins, vitamins, minerals, fiber, fatty acids, amino acids and proteins.

In a specific configuration, the preparation further comprises vitamins selected from biotin, vitamin A, vitamin B1 (thiamine), vitamin B2 (riboflavin), vitamin B3 (niacin), vitamin B5 (pantothenic acid), vitamin B9 (folic acid or folate), vitamin C (ascorbic acid), vitamin D (calciferols), vitamin E (tocopherols and tocotrienols) and vitamin K (quinones) or minerals selected from sulfur, iron, chlorine, calcium, chromium, cobalt, copper, magnesium, manganese, molybdenum, iodine, selenium, and zinc.

A further aspect of the present invention is related to a tablet, pellet, microparticle or microparticulate composition or capsule comprising a preparation according to the present invention.

In a specific combination, the present invention relates to a capsule comprising a preparation according to the present invention. The capsule may comprise up to 50% by weight of both extract of gum resins from *Boswellia* species and polyunsaturated fatty acid salt. The polyunsaturated fatty acid salt comprises at least one omega-3 fatty acid selected from eicosapentaenoic acid (EPA) and docosahexaenoic acid (DHA) and at least one basic amino acid. The basic amino acid is preferably selected form lysine, arginine and ornithine.

In a further specific combination, the present invention relates to a tablet comprising a preparation according to the present invention. The tablet comprises at least 20% by weight of the extract of gum resins from *Boswellia* species and at least 20% by weight of polyunsaturated fatty acid salt. The polyunsaturated fatty acid salt comprises at least one omega-3 fatty acid selected from eicosapentaenoic acid (EPA) and docosahexaenoic acid (DHA) and at least one basic amino acid. The basic amino acid is preferably selected form lysine, arginine and ornithine.

Moreover, the use of such a preparation as a feed or food supplement or as pharmaceutical product or in topical applications is part of the present invention.

Another aspect of the present invention is a preparation as described above for use in the treatment or prevention of chronic inflammatory diseases, preferably asthma, occupational asthma, eczema, bronchitis, hay fever, hives, rheumatoid arthritis, juvenile rheumatoid arthritis, psoriatic arthritis, osteoarthritis, refractory rheumatoid arthritis, chronic non-rheumatoid arthritis, osteoporosis, coronary heart disease, atherosclerosis, endothelial dysfunction, multiple sclerosis, vasculitis, nephritis, uveitis, glomerulonephritis, systemic lupus erythematosis, post-angioplasty restenosis, ulcerative colitis, conjunctivitis, dermatitis, psoriasis, cystic fibrosis, adult respiratory distress syndrome, IBS (inflammatory bowel syndrome), IBD (inflammatory bowel disease), chronic obstructive pulmonary disease, adult respiratory distress syndrome, allergic rhinitis, gastrointestinal allergies, allergic disorders, lichen simplex chronicus (LSC).

A further aspect of the present invention is related to a preparation comprising at least one *Boswellia* extract and at least one polyunsaturated fatty acid salt comprising at least one omega-3 fatty acid selected from eicosapentaenoic acid (EPA) and docosahexaenoic acid (DHA) and at least one basic amino acid for use to increase the formation of one or more specialized pro-resolving lipid mediators (SPM).

The SPMs are preferably selected from 17-hydroxy-DHA (17-HDHA), 14-hydroxy-DHA (14-HDHA), 13-hydroxy-DHA (13-HDHA), 7-hydroxy-DHA (7-HDHA), 4-hydroxy-DHA (4-HDHA), 18-hydroxy-eicosapentaenoic acid (18-HEPE), 15-hydroxy-eicosapentaenoic acid (15-HEPE), 12-hydroxy-eicosapentaenoic acid (12-HEPE), 11-hydroxy-eicosapentaenoic acid (11-HEPE), 8-hydroxy-eicosapentaenoic acid (8-HEPE), 5-hydroxy-eicosapentaenoic acid (5-HEPE), 15-hydroxy-eicosatetraenoic acid (15-HETE), 12-hydroxy-eicosatetraenoic acid (12-HETE), 8-hydroxy-eicosatetraenoic acid (8-HETE), 5-hydroxy-eicosatetraenoic acid (5-HETE), 9-hydroxyoctadecadienoic acid (9-HODE), 13-hydroxyoctadecadienoic acid (13-HODE), 10(S),17(S)-dihydroxy-docosahexaenoic acid (PDX), protectin D1 (PD1), Aspirin-triggered PD1 (AT-PD1), maresin 1 (MaR1), maresin 2 (MaR2), resolvin D1-6 (RvD1-6), Aspirin-triggered RvD1 (AT-RvD1), resolvin E1 (RvE1), resolvin E2 (RvE2) resolvin E3 (RvE3), lipoxin $A_4$ (LXA$_4$), lipoxin $A_5$ (LXA$_5$), lipoxin $B_4$ (LXB$_4$), lipoxin $B_5$ (LXB$_5$), Therefore, in a further preferred embodiment the SPM is selected from 17-HDHA, 14-HDHA, 13-HDHA, 7-HDHA, 4-HDHA, 18-HEPE, 15-HEPE, 12-HEPE, 11-HEPE, 5-HEPE, 15-HETE, 12-HETE, 8-HETE, 5-HETE, 9-NODE, 13-NODE, PDX, PD1, AT-PD1, MaR1, MaR2, RvD1-6, AT-RvD1, RvE1, RvE2, RvE3, LXA4, LXA5, LXB4, LXB5, preferably from 17-HDHA, 14-HDHA, 18-HEPE, PDX, PD1, RvD1-6, MaR1.

WORKING EXAMPLES

Isolation and Incubations of Macrophages, and LM Metabololipidomics

Leukocyte concentrates from freshly withdrawn peripheral blood of healthy adult human donors were provided by the Institute of Transfusion Medicine, University Hospital Jena, Germany. The experimental protocol was approved by the ethical committee of the University Hospital Jena. All methods were performed in accordance with the relevant guidelines and regulations. Peripheral blood mononuclear cells (PBMC) were isolated using dextran sedimentation and Ficoll-Histopaque 1077-1 (Sigma-Aldrich, Taufkirchen, Germany) centrifugation. For differentiation and polarization towards M1 and M2, published criteria were used [32]. Thus, M1 were generated by incubating monocytes with 20 ng/ml GM-CSF (Peprotech, Hamburg, Germany) for 6 days in RPMI 1640 supplemented with 10% fetal calf serum, 2 mmol/L 1-glutamine (Biochrom/Merck, Berlin, Germany), and penicillin-streptomycin (Biochrom/Merck), followed by 100 ng/ml LPS (Sigma-Aldrich) and 20 ng/ml INF-γ (Peprotech) treatment for another 48 h. M2 were incubated with 20 ng/ml M-CSF (Peprotech) for 6 days of differentiation plus 20 ng/ml IL-4 (Peprotech) for additional 48 h of polarization.

Macrophages (2×10$^6$/ml) were incubated in PBS containing 1 mM CaCl$_2$). Extracts of *Boswellia serrata* or vehicle control (0.1% DMSO) were applied 15 min prior to stimulation with *E. coli* (serotype O6:K2:H1) at a ratio of 1:50 (M1/M2:*E. coli*) for 180 min at 37° C. Supernatants were transferred to 2 ml of ice-cold methanol containing 10 μl of deuterium-labeled internal standards (200 nM da-55-HETE, d$_4$-LTB$_4$, d$_5$-LXA$_4$, d$_5$-RvD2, d$_4$-PGE$_2$ and 10 μM d$_8$-AA) to facilitate quantification. Deuterated and non-deuterated LM standards were purchased from Cayman Chemical/Biomol GmbH (Hamburg, Germany). Sample preparation was conducted by adapting published criteria [33]. In brief, samples were kept at −20° C. for 60 min to allow protein precipitation. After centrifugation (1200 g, 4° C., 10 min) 8 ml acidified H$_2$O (pH 3.5) was added and subjected to solid phase extraction. Solid phase cartridges (Sep-Pak® Vac 6 cc 500 mg/6 ml C18; Waters, Milford, MA) were equilibrated with 6 ml methanol and 2 ml $H_2O$ before samples were loaded onto columns. After washing with 6 ml $H_2O$ and additional 6 ml n-hexane, LM were eluted with 6 ml methyl formiate. Finally, the samples were brought to dryness using an evaporation system (TurboVap LV, Biotage, Uppsala, Sweden) and resuspended in 100 µl methanol-water (50/50, v/v) for UPLC-MS-MS automated injections. LM profiling was analyzed with an Acquity™ UPLC system (Waters, Milford, MA) and a QTRAP 5500 Mass Spectrometer (ABSciex, Darmstadt, Germany) equipped with a Turbo VTM Source and electrospray ionization (ESI). LM were eluted using an ACQUITY UPLC® BEH C18 column (1.7 µm, 2.1×100 mm; Waters, Eschborn, Germany) at 50° C. with a flow rate of 0.3 ml/min and a mobile phase consisting of methanol-water-acetic acid of 42:58:0.01 (v/v/v) that was ramped to 86:14:0.01 (v/v/v) over 12.5 min and then to 98:2:0.01 (v/v/v) for 3 min (Table 51). The QTrap 5500 was operated in negative ionization mode using scheduled multiple reaction monitoring (MRM) coupled with information-dependent acquisition. The scheduled MRM window was 60 sec, optimized LM parameters (CE, EP, DP, CXP) were adopted [33], and the curtain gas pressure was set to 35 psi. The retention time and at least six diagnostic ions for each LM were confirmed by means of an external standard (Cayman Chemicals). Quantification was achieved by calibration curves for each LM. Linear calibration curves were obtained for each LM and gave $r^2$ values of 0.998 or higher (for fatty acids 0.95 or higher).

Polyunsaturated Fatty Acid Compositions

In the examples for the present invention, different polyunsaturated fatty acid compositions were used. Different omega-3 fatty acid salts having an organic counter ion selected from the basic amino acids lysine, arginine and ornithine were prepared. The omega-3 fatty acids Eicosapentaenoic acid (C20:5w3c) (EPA) and Docosahexaenoic acid (C22:6w3c) (DHA) are present in a ratio of around 2:1 (ratio EPA: DHA).

The omega-3 lysine salt (AvailOm®) contains around 32 weight-% of L-lysine and around 65 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 58 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

The omega-3 arginine salt (omega-3-arg) contains around 35 weight-% of L-arginine and around 64 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 49 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

The omega-3 ornithine salt (omega-3-orn) contains around 29 weight-% of L-ornithine and around 70 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 54 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

Example 1: Extracts of Gum Resins from *Boswellia* Species Stimulate LM Biosynthesis Formation in *E. coli*-Stimulated Human Monocyte-Derived M1 and M2 Macrophages Human monocyte-derived macrophages were polarized for 48 hrs to M1 (FIG. 1) or to M2 (FIG. 2) subtypes and subsequently incubated with extracts of gum resins from *Boswellia* species (*Boswellia* extracts) BS (Boswellin Super®, Sabinsa Corporation, USA, a standardized extract from the gum resin of *B. serrata* containing min. 10% AKBA, total identified boswellic acids min. 20%), CAS (Casperome®, Indena, a purified extract, obtained from the gum resin of *Boswellia serrata*, containing ≥25% boswellic acids), and AUR (Aureliasan extract, a *Boswellia carterii* extract) (50 µg/mL, each) or AKBA (10 µM) supplemented with (grey bars) or without AvailOm® (3 µg/mL, black bars). After 180 min incubation at 37° C., lipid mediators were isolated by solid phase extraction and analyzed by UPLC-MS-MS. Data are means±S.E.M., n=3. One way ANOVA with log transformed data was performed (Tukey post-hoc test; *, #p<0.05; , ##p<0.01; *, ###p<0,005).

Formation of the LM RvD2, RvD4, RvD5, PDX, PD1, MaR1, 17-HDHA, 14-HDHA, 18-HEPE and $LTB_4$ and $PGE_2$ in M1 macrophages is shown in FIG. 1 and in M2 macrophages in shown in FIG. 2.

In pro-inflammatory M1 macrophages that usually produce low amounts of SPM, the addition of AvailOm® caused only weak increases in LM formation, and also exposure to *Boswellia* extracts (AUR, BS or CAS) or AKBA did not significantly elevate LM biosynthesis. However, the combination of AvailOm® with *Boswellia* extracts or AKBA induced significant elevation of EPA- and DHA-derived LM, particularly of RvD5, PD1, PDX, MaR1 and 18-HEPE. In contrast, AA-derived pro-inflammatory LM (PGE2 and LTB4) were not increased under any condition. These data suggest that AvailOm® causes a switch of LM formation in M1 from pro-inflammatory to pro-resolving character.

More striking effects by the combination of AvailOm® and *Boswellia* extracts (AUR, BS or CAS) or AKBA on EPA- and DHA-derived LM production was evident in M2 (FIG. 2). Surprisingly, while either the *Boswellia* extracts or AvailOm® had moderate effects, the combination clearly yielded synergistic elevation of lipid mediators, for example for RvD5, PD1, PDX and the precursor 17-HDHA; the same applies to MaR1 and 14-HDHA. The data suggest a synergistic mechanism of SPM formation where *Boswellia* extracts activate the key enzyme 15-LOX-1 and where AvailOm® serves as available substrate. Supplementation of EPA and/or DHA as substrate (AvailOm®) alone is however not sufficient to induce substantial SPM formation as compared to the combination with *Boswellia* extracts.

It can be concluded that supplementation of human M1 and M2 macrophages with AvailOm® in vitro promotes the formation of SPM and their precursors, particularly when cells were activated with AKBA, a pharmacological anti-inflammatory agent, or with *Boswellia* extracts. These data strongly suggest to combine AKBA or parental *Boswellia* extracts with AvailOm® to promote formation of pro-resolving LM (i.e. SPM) and consequently to resolve inflammatory disorders.

Example 2: Effects of EPA/DHA Lys-Salt and Free Fatty Acids on Lipid Mediator Biosynthesis Formation in Human Monocyte-Derived M1 and M2 Macrophages Human monocyte-derived macrophages were polarized for 48 hrs to M1 (FIG. 3) or to M2 (FIG. 4) subtypes and subsequently incubated with different sources for omega-3 fatty acids: Omegatex (Omegatex5723, 57% EPA, 23% DHA), Omega3 (Omega-3-fatty acid, 57% EPA, 23% DHA), AvailOm®, and liposomal AvailOm® (corresponding to 3 µg/ml EPA plus DHA) supplemented with (grey bars) or without *Boswellia* extract AUR (50 µg/mL, black bars). After 180 min incubation at 37° C., lipid mediators were isolated by solid phase extraction and analyzed by UPLC-MS-MS. Data are means±S.E.M., n=3. One way ANOVA with log transformed data was performed (Tukey post-hoc test; *, #p<0.05; , ##p<0.01; *, ###p<0,005).

Formation of the LM RvD2, RvD4, RvD5, PDX, PD1, MaR1, 17-HDHA, 14-HDHA, 18-HEPE and LTB$_4$ and PGE$_2$ in M1 macrophages is shown in FIG. 3 and in M2 macrophages in shown in FIG. 4.

Comparison of various sources of DHA and EPA as substrates for SPM/precursors upon supplementation of macrophages showed that in M1, AvailOm® in combination with *Boswellia* extract AUR caused most prominent elevation of RvD5, PD1, PDX, MaR1, and 14-HDHA, followed by liposomal AvailOm® that gave highest 17-HDHA formation with AUR (FIG. 3). Again, AvailOm® and AUR in combination caused synergistic effects for RvD5, PD1, PDX, MaR1, 17-HDHA and 14-HDHA but no stimulatory effects were evident for AA-derived PGE2 and LTB4.

In M2 that in general possess higher capacities for SPM production due to the high expression levels of SPM-biosynthetic key enzyme 15-LOX-1, *Boswellia* extract AUR strongly elevated all investigated SPM and precursors (FIG. 4) in combination with Omega3, AvailOm®, or liposomal AvailOm®. Again, only moderate effects of either AUR or Omega3, AvailOm®, and liposomal AvailOm® or combinations thereof were evident for LTB4 and PGE2 formation.

Example 3: Effects of EPA/DHA Lys-Salt and Free Fatty Acids on Lipid Mediator Biosynthesis Formation in Human Monocyte-Derived M1 and M2 Macrophages Human monocyte-derived macrophages were polarized for 48 hrs to M2 subtypes and subsequently incubated with different omega-3 fatty acid salts: omega-3 lysine salt (AvailOm®), omega-3 arginine salt and omega-3 ornithine salt and supplemented with (grey bars) or without *Boswellia* extract AUR (50 µg/mL, black bars). After 180 min incubation at 37° C., lipid mediators were isolated by solid phase extraction and analyzed by UPLC-MS-MS. Data shown in FIGS. 5 and 6 are means±S.E.M., n=3. One way ANOVA with log transformed data was performed (Tukey post-hoc test; *, #p<0.05; , ##p<0.01; *, ###p<0,005).

Table 1 summarizes the values for the stimulation of LM biosynthesis formation in human M2 macrophages by *Boswellia* extract AUR and lysine salts of EPA and DHA (AvailOm®) in µg/million cells, table 2 for the arginine salts of EPA and DHA and table 3 for the ornithine salts of EPA and DHA. The values "-fold" refer to the relative fold increase in comparison to the *Boswellia* extract.

Those values clearly show that for all three omega-3 salts, there is a synergistic effect with the *Boswellia* extract on the production of SPM, as the measured values for the combination product is much higher than the sum of the values for the single substances. For example, for all the amino acid salts this effect is drastic referring to the SPMs 17-HDHA, 14-HDHA, 7-HDHA, 4-HDHA, 18-HEPE, 15-HEPE, 12-HEPE, 11-HEPE, 5-HEPE.

TABLE 1

Stimulation of LM biosynthesis formation in human M2 macrophages by Boswellia extract AUR and lysine salts of EPA and DHA (AvailOm ®), values correspond to pg/million cells

|  | veh. | lysine salt | Bosw. extr. | Bosw. extr. + lysine salt | -fold |
|---|---|---|---|---|---|
| RvD1 | 1.0 ± 0.3 | 7 ± 2.6 | 2.0 ± 0.2 | 8 ± 2.7 | 3.8 |
| RvD2 | 0.4 ± 0.1 | 4.4 ± 2.2 | 0.8 ± 0.1 | 5 ± 2.4 | 6.9 |
| RvD5 | 1.0 ± 0.3 | 73 ± 57 | 3.7 ± 3.5 | 151 ± 111 | 40.8 |
| RvD6 | 7 ± 0.6 | 13 ± 3.9 | 6 ± 0.2 | 23 ± 5 | 3.8 |
| MaR1 | 0.3 ± 0.1 | 28 ± 16 | 0.3 ± 0.1 | 44 ± 17 | 136.6 |
| PD1 | 1.4 ± 0.3 | 144 ± 36 | 2.2 ± 1.5 | 253 ± 27 | 116.8 |
| AT-PD1 | 2.5 ± 0.3 | 134 ± 13 | 3.3 ± 0.5 | 204 ± 7 | 62.2 |
| PDX | 0.7 ± 0.0 | 27 ± 10 | 1.0 ± 0.3 | 40 ± 6 | 40.9 |
| RvE3 | 1.8 ± 0.8 | 85 ± 9 | 2.6 ± 0.9 | 94 ± 3.0 | 36.0 |
| LXA4 | 0.3 ± 0.1 | 4.5 ± 1.3 | 2.9 ± 0.8 | 8 ± 1.8 | 2.7 |
| 5.15-diHETE | 4.4 ± 0.5 | 29 ± 9 | 10 ± 4.3 | 49 ± 24 | 5.1 |
| LTB4 | 3.4 ± 0.4 | 11 ± 3.9 | 4.5 ± 0.6 | 17 ± 3.8 | 3.8 |
| t-LTB4 | 3.5 ± 0.8 | 22 ± 5 | 4.6 ± 0.5 | 34 ± 1.9 | 7.4 |
| 20-OH-LTB4 | 0.7 ± 0.1 | 14 ± 0.3 | 3.5 ± 0.2 | 19 ± 0.4 | 5.3 |
| PGD2 | 4.0 ± 1.3 | 11 ± 5 | 13 ± 2.1 | 27 ± 7 | 2.0 |
| PGE2 | 11 ± 2.0 | 36 ± 10 | 38 ± 6 | 97 ± 15 | 2.6 |
| PGF2a | 21 ± 3.1 | 43 ± 10 | 50 ± 3.2 | 68 ± 7 | 1.4 |
| TXB2 | 268 ± 129 | 421 ± 250 | 569 ± 243 | 486 ± 274 | 0.9 |
| 17-HDHA | 54 ± 38 | 3424 ± 1985 | 188 ± 144 | 6047 ± 2171 | 32.1 |
| 14-HDHA | 8 ± 2.8 | 1054 ± 477 | 31 ± 14 | 2141 ± 410 | 69.1 |
| 7-HDHA | 7 ± 1.2 | 1053 ± 149 | 10 ± 2.2 | 1402 ± 23 | 134.5 |
| 4-HDHA | 6 ± 2.0 | 663 ± 163 | 13 ± 3.7 | 853 ± 7 | 64.5 |
| 18-HEPE | 8 ± 2.6 | 14340 ± 1429 | 14 ± 2.1 | 18472 ± 371 | 1325.6 |
| 15-HEPE | 15 ± 9 | 4557 ± 3167 | 37 ± 28 | 9114 ± 4078 | 244.1 |
| 12-HEPE | 1.9 ± 0.9 | 2927 ± 1199 | 8 ± 2.1 | 6038 ± 907 | 782.9 |

TABLE 1-continued

Stimulation of LM biosynthesis formation in human M2 macrophages
by Boswellia extract AUR and lysine salts of EPA and DHA
(AvailOm ®), values correspond to pg/million cells

|  | veh. | lysine salt | Bosw. extr. | Bosw. extr. + lysine salt | -fold |
|---|---|---|---|---|---|
| 11-HEPE | 2.5 ± 1.3 | 3644 ± 800 | 7 ± 1.5 | 6556 ± 118 | 934.4 |
| 5-HEPE | 3.8 ± 1.3 | 5272 ± 867 | 7 ± 0.9 | 7802 ± 379 | 1090.2 |
| 15-HETE | 21 ± 12 | 925 ± 695 | 206 ± 155 | 2064 ± 1159 | 10.0 |
| 12-HETE | 7 ± 1.7 | 174 ± 90 | 64 ± 3.4 | 334 ± 132 | 5.3 |
| 11-HETE | 3.4 ± 1.4 | 223 ± 47 | 26 ± 6 | 426 ± 13 | 16.4 |
| AA | 2552 ± 733 | 65339 ± 11504 | 18222 ± 3471 | 115317 ± 9345 | 6.3 |
| EPA | 2834 ± 1328 | 57083 ± 5768 | 5039 ± 1237 | 79805 ± 14232 | 15.8 |
| DHA | 8242 ± 3481 | 71168 ± 8521 | 15765 ± 4058 | 107948 ± 13000 | 6.8 |

TABLE 2

Stimulation of LM biosynthesis formation in human M2 macrophages
by Boswellia extract AUR and arginine salts of EPA and
DHA, values correspond to pg/million cells

|  | veh. | arginine salt | Bosw. extr. | Bosw. extr. + arginine salt | -fold |
|---|---|---|---|---|---|
| RvD1 | 1.0 ± 0.3 | 2.3 ± 0.4 | 2.0 ± 0.2 | 4.6 ± 1.2 | 2.3 |
| RvD2 | 0.4 ± 0.1 | 0.8 ± 0.1 | 0.8 ± 0.1 | 2.9 ± 1.5 | 3.7 |
| RvD5 | 1.0 ± 0.3 | 1.4 ± 0.4 | 3.7 ± 3.5 | 67 ± 64 | 18.1 |
| RvD6 | 7 ± 0.6 | 7.6 ± 0.3 | 6 ± 0.2 | 8 ± 2.1 | 1.3 |
| MaR1 | 0.3 ± 0.1 | 0.4 ± 0.2 | 0.3 ± 0.1 | 12 ± 11 | 38.6 |
| PD1 | 1.4 ± 0.3 | 7 ± 2.1 | 2.2 ± 1.5 | 26 ± 17 | 12.2 |
| AT-PD1 | 2.5 ± 0.3 | 7 ± 0.8 | 3.3 ± 0.5 | 18 ± 5 | 5.6 |
| PDX | 0.7 ± 0.0 | 1.3 ± 0.3 | 1.0 ± 0.3 | 6 ± 4.1 | 6.3 |
| RvE3 | 1.8 ± 0.8 | 29 ± 2.5 | 2.6 ± 0.9 | 23 ± 2.5 | 9.0 |
| LXA4 | 0.3 ± 0.1 | 1.2 ± 0.1 | 2.9 ± 0.8 | 4.9 ± 1.3 | 1.7 |
| 5.15-diHETE | 4.4 ± 0.5 | 6 ± 1.1 | 10 ± 4.3 | 32 ± 24 | 3.3 |
| LTB4 | 3.4 ± 0.4 | 4.3 ± 0.4 | 4.5 ± 0.6 | 10 ± 6 | 2.3 |
| t-LTB4 | 3.5 ± 0.8 | 4.9 ± 0.4 | 4.6 ± 0.5 | 11 ± 3.3 | 2.4 |
| 20-OH-LTB4 | 0.7 ± 0.1 | 3.0 ± 0.3 | 3.5 ± 0.2 | 6 ± 0.2 | 1.7 |
| PGD2 | 4.0 ± 1.3 | 3.3 ± 0.4 | 13 ± 2.1 | 20 ± 8 | 1.5 |
| PGE2 | 11 ± 2.0 | 14 ± 2.1 | 38 ± 6 | 54 ± 15 | 1.4 |
| PGF2a | 21 ± 3.1 | 20 ± 5 | 50 ± 3.2 | 62 ± 10 | 1.2 |
| TXB2 | 268 ± 129 | 173 ± 43 | 569 ± 243 | 548 ± 282 | 1.0 |
| 17-HDHA | 54 ± 38 | 188 ± 33 | 188 ± 144 | 1185 ± 935 | 6.3 |
| 14-HDHA | 8 ± 2.8 | 64 ± 9 | 31 ± 14 | 310 ± 220 | 10.0 |
| 7-HDHA | 7 ± 1.2 | 84 ± 15 | 10 ± 2.2 | 198 ± 49 | 19.0 |
| 4-HDHA | 6 ± 2.0 | 139 ± 20 | 13 ± 3.7 | 223 ± 27 | 16.8 |
| 18-HEPE | 8 ± 2.6 | 941 ± 140 | 14 ± 2.1 | 1499 ± 149 | 107.6 |
| 15-HEPE | 15 ± 9 | 74 ± 16 | 37 ± 28 | 1401 ± 1209 | 37.5 |
| 12-HEPE | 1.9 ± 0.9 | 115 ± 20 | 8 ± 2.1 | 563 ± 292 | 73.0 |
| 11-HEPE | 2.5 ± 1.3 | 135 ± 27 | 7 ± 1.5 | 520 ± 78 | 74.1 |
| 5-HEPE | 3.8 ± 1.3 | 513 ± 124 | 7 ± 0.9 | 1103 ± 85 | 154.2 |
| 15-HETE | 21 ± 12 | 39 ± 19 | 206 ± 155 | 897 ± 793 | 4.4 |
| 12-HETE | 7 ± 1.7 | 23 ± 1.8 | 64 ± 3.4 | 139 ± 81 | 2.2 |
| 11-HETE | 3.4 ± 1.4 | 19 ± 3.3 | 26 ± 6 | 87 ± 29 | 3.3 |
| AA | 2552 ± 733 | 17169 ± 2186 | 18222 ± 3471 | 69716 ± 12350 | 3.8 |
| EPA | 2834 ± 1328 | 41966 ± 1104 | 5039 ± 1237 | 64639 ± 9735 | 12.8 |
| DHA | 8242 ± 3481 | 44473 ± 1803 | 15765 ± 4058 | 71498 ± 11435 | 4.5 |

TABLE 3

Stimulation of LM biosynthesis formation in human M2 macrophages
by Boswellia extract AUR and ornithine salts of EPA and
DHA, values correspond to pg/million cells

|  | veh. | ornithine salt | Bosw. extr. | Bosw. extr. + ornithine salt | -fold |
|---|---|---|---|---|---|
| RvD1 | 1.0 ± 0.3 | 2.1 ± 0.1 | 2.0 ± 0.2 | 2.2 ± 0.5 | 1.1 |
| RvD2 | 0.4 ± 0.1 | 1.0 ± 0.0 | 0.8 ± 0.1 | 1.5 ± 0.6 | 1.9 |
| RvD5 | 1.0 ± 0.3 | 1.2 ± 0.4 | 3.7 ± 3.5 | 26 ± 23 | 6.9 |

TABLE 3-continued

Stimulation of LM biosynthesis formation in human M2 macrophages by Boswellia extract AUR and ornithine salts of EPA and DHA, values correspond to pg/million cells

|  | veh. | ornithine salt | Bosw. extr. | Bosw. extr. + ornithine salt | -fold |
|---|---|---|---|---|---|
| RvD6 | 7 ± 0.6 | 7 ± 0.4 | 6 ± 0.2 | 6 ± 0.4 | 1.0 |
| MaR1 | 0.3 ± 0.1 | 0.1 ± 0.0 | 0.3 ± 0.1 | 3.2 ± 2.9 | 9.9 |
| PD1 | 1.4 ± 0.3 | 2.3 ± 0.8 | 2.2 ± 1.5 | 9 ± 5 | 4.2 |
| AT-PD1 | 2.5 ± 0.3 | 3.3 ± 0.1 | 3.3 ± 0.5 | 8 ± 2.2 | 2.5 |
| PDX | 0.7 ± 0.0 | 0.9 ± 0.2 | 1.0 ± 0.3 | 2.7 ± 1.4 | 2.7 |
| RvE3 | 1.8 ± 0.8 | 8 ± 0.8 | 2.6 ± 0.9 | 6 ± 1.4 | 2.2 |
| LXA4 | 0.3 ± 0.1 | 0.4 ± 0.1 | 2.9 ± 0.8 | 3.6 ± 0.5 | 1.3 |
| 5.15-diHETE | 4.4 ± 0.5 | 4.2 ± 0.8 | 10 ± 4.3 | 17 ± 9 | 1.8 |
| LTB4 | 3.4 ± 0.4 | 3.9 ± 0.2 | 4.5 ± 0.6 | 6 ± 1.9 | 1.4 |
| t-LTB4 | 3.5 ± 0.8 | 4.8 ± 0.5 | 4.6 ± 0.5 | 6 ± 1.2 | 1.4 |
| 20-OH-LTB4 | 0.7 ± 0.1 | 1.2 ± 0.1 | 3.5 ± 0.2 | 3.8 ± 0.4 | 1.1 |
| PGD2 | 4.0 ± 1.3 | 3.4 ± 0.8 | 13 ± 2.1 | 21 ± 4.9 | 1.5 |
| PGE2 | 11 ± 2.0 | 12 ± 2.2 | 38 ± 6 | 40 ± 7 | 1.1 |
| PGF2a | 21 ± 3.1 | 24 ± 8 | 50 ± 3.2 | 59 ± 13 | 1.2 |
| TXB2 | 268 ± 129 | 220 ± 56 | 569 ± 243 | 627 ± 372 | 1.1 |
| 17-HDHA | 54 ± 38 | 117 ± 38 | 188 ± 144 | 497 ± 354 | 2.6 |
| 14-HDHA | 8 ± 2.8 | 31 ± 3.0 | 31 ± 14 | 120 ± 75 | 3.9 |
| 7-HDHA | 7 ± 1.2 | 38 ± 3.8 | 10 ± 2.2 | 77 ± 12 | 7.4 |
| 4-HDHA | 6 ± 2.0 | 35 ± 7 | 13 ± 3.7 | 62 ± 9 | 4.7 |
| 18-HEPE | 8 ± 2.6 | 406 ± 56 | 14 ± 2.1 | 591 ± 44 | 42.4 |
| 15-HEPE | 15 ± 9 | 57 ± 19 | 37 ± 28 | 551 ± 440 | 14.8 |
| 12-HEPE | 1.9 ± 0.9 | 51 ± 8 | 8 ± 2.1 | 204 ± 94 | 26.4 |
| 11-HEPE | 2.5 ± 1.3 | 56 ± 12 | 7 ± 1.5 | 176 ± 22 | 25.1 |
| 5-HEPE | 3.8 ± 1.3 | 157 ± 34 | 7 ± 0.9 | 296 ± 24 | 41.4 |
| 15-HETE | 21 ± 12 | 22 ± 8 | 206 ± 155 | 358 ± 284 | 1.7 |
| 12-HETE | 7 ± 1.7 | 21 ± 6 | 64 ± 3.4 | 55 ± 32 | 0.9 |
| 11-HETE | 3.4 ± 1.4 | 8 ± 1.9 | 26 ± 6 | 40 ± 11 | 1.5 |
| AA | 2552 ± 733 | 15574 ± 2895 | 18222 ± 3471 | 53632 ± 5295 | 2.9 |
| EPA | 2834 ± 1328 | 45097 ± 1406 | 5039 ± 1237 | 65206 ± 10780 | 12.9 |
| DHA | 8242 ± 3481 | 47473 ± 2492 | 15765 ± 4058 | 69161 ± 9918 | 4.4 |

The formation of the LM RvD2, RvD4, RvD5, PDX, PD1, MaR1, 17-HDHA, 14-HDHA, 18-HEPE and LTB$_4$ and PGE$_2$ in M2 macrophages for omega-3 lysine (AvailOm®), arginine and ornithine salts are shown in FIG. 5.

FIG. 6 shows the stimulation of LM biosynthesis formation in human M2 macrophages for omega-3 arginine and ornithine salts.

Example 4: Capsule Comprisinq EPA/DHA Lys-Salt and *Boswellia* Extract

The following components were filled in HPMC capsules:

TABLE 4

Preparations for filling into HPMC capsules.

| Compound | Capsule I | Capsule II | Capsule III |
|---|---|---|---|
| Omega-3 lysine salt (AvailOm ®) | 400 mg | 200 mg | 50 mg |
| *Boswellia* extract | 400 mg | 200 mg | 50 mg |

The capsules may further contain amino acids selected from L-ornithine, L-aspartate, L-lysine and L-arginine. The capsules may further contain further carbohydrate ingredients, selected from arabinoxylans, barley grain fibre, oat grain fibre, rye fibre, wheat bran fibre, inulins, fructooligosaccharides (FOS), galactooligosaccharides (GOS), resistant starch, beta-glucans, glucomannans, galactoglucomannans, guar gum and xylooligosaccharides.

The capsules may further contain one or more plant extracts, selected from ginger, cinnamon, grapefruit, parsley, turmeric, *curcuma*, olive fruit, *panax ginseng*, horseradish, garlic, broccoli, *spirulina*, pomegranate, cauliflower, kale, cilantro, green tea, onions, and milk thistle. The capsules may further contain charcoal, chitosan, glutathione, monacolin K, plant sterols, plant stanols, sulforaphane, collagen, hyalurone. The capsules may comprise further vitamins selected from biotin, vitamin A, vitamin B1 (thiamine), vitamin B2 (riboflavin), vitamin B3 (niacin), vitamin B5 (pantothenic acid), vitamin B9 (folic acid or folate), vitamin C (ascorbic acid), vitamin D (calciferols), vitamin E (tocopherols and tocotrienols) and vitamin K (quinones) or minerals selected from sulfur, iron, chlorine, calcium, chromium, cobalt, copper, magnesium, manganese, molybdenum, iodine, selenium, and zinc.

Example 5: Enteric Delivery Capsule Comprising EPA/DHA Lys-Salt and *Boswellia* Extract The capsules as prepared in example 3 were coated with an enteric coating composition:

TABLE 5

Coating composition

| Compound | Dry substance [g] | Content based on coating [%] | Weight gain [%] | Content based on capsule [%] |
|---|---|---|---|---|
| EUDRAGUARD ® biotic | 40.8 | 36.9 | 8.2 | 6.7 |
| HPMC | 43.1 | 39.0 | 8.6 | 7.1 |
| Talc | 20.4 | 18.4 | 4.0 | 3.3 |
| Polyethylene glycol | 4.3 | 3.9 | 0.9 | 0.7 |
| Triethyl citrate | 2.0 | 1.8 | 0.4 | 0.3 |

Example 6: Tablet Formulation Comprising EPA/DHA Lys-Salt and *Boswellia* Extract A formulation (table 6) was prepared and used for tableting. The tablet core components (except magnesium stearate) at their corresponding mass in the respective formulation were blended by the use of a turbola blender. Magnesium stearate was added in a second blending step just before the compression process.

TABLE 6

Preparation for preparation of tablets

| Substance | Content [weight-%] |
|---|---|
| AvailOm ® | 25 |
| Phospholipids (Lipoid H 20) | 12.9 |
| *Boswellia serrata* extract (AureliaSan) | 12.5 |
| Dicalcium phosphate anh. (Cafos N201) | 19 |
| Micro crystalline cellulose (Avicel 200) | 20 |
| Croscarmellose-Na (Ac-Di-Sol SD 711) | 2.6 |
| Magnesium stearate | 3 |
| Crospovidone (Polyplasdone XL) | 5 |
| Sum total | 100 |

Tablet compression was conducted on a Korsch XP 1 eccentric press. A 21 mm×9 mm oval biconvex tooling was used to gain tablets of a target weight of 1000 mg. A compression force of approx. 15 kN resulted in tablets of a hardness (resistance to crushing) of approx. 75N. The friability was below 1% and the uniformity of mass showed variation less than 5%.

As a final production step, the resulting tablets are coated with a EUDRUARD Natural based coating. The coating provides a taste- and odor masking as well as a barrier against moisture uptake and can improve photostability. The coating was conducted on a O'Hara Labcoat drum coater with a perforated 15" drum. 4.0 mg/cm$^2$ of the coating suspension consisting of EUDRAGUARD Natural, Talc, Glycerol and Chlorophyll E 141 ii were applied at an average spraying rate of 5.5 g/min/kg.

The resulting film coated tablets were intact and non-aggregated. The characteristic smell of AvailOm® and *Boswelia serrata* extract was significantly masked. The film coated tablets disintegrated in 0.1 N HCl pH 1.20 within 30 min, provided a uniformity of mass with a variation less than 5%, and the water content was between 4-7%.

The compressed tablets were stable for at least two months at 25° C. and 60% relative humidity and at 40° C. and 75% relative humidity.

The tablet may comprise further vitamins selected from biotin, vitamin A, vitamin B1 (thiamine), vitamin B2 (riboflavin), vitamin B3 (niacin), vitamin B5 (pantothenic acid), vitamin B9 (folic acid or folate), vitamin C (ascorbic acid), vitamin D (calciferols), vitamin E (tocopherols and tocotrienols) and vitamin K (quinones) or minerals selected from sulfur, iron, chlorine, calcium, chromium, cobalt, copper, magnesium, manganese, molybdenum, iodine, selenium, and zinc.

REFERENCES

1. Balk E M, Lichtenstein A H: Omega-3 Fatty Acids and Cardiovascular Disease: Summary of the 2016 Agency of Healthcare Research and Quality Evidence Review. *Nutrients* 2017, 9(8).
2. Calder P C: Marine omega-3 fatty acids and inflammatory processes: Effects, mechanisms and clinical relevance. *Biochim Biophys Acta* 2015, 1851(4):469-484.
3. Papanikolaou Y, Brooks J, Reider C, Fulgoni V L, 3rd: U.S. adults are not meeting recommended levels for fish and omega-3 fatty acid intake: results of an analysis using observational data from NHANES 2003-2008. *Nutr J* 2014, 13:31.
4. Clarke T C, Black L I, Stussman B J, Barnes P M, Nahin R L: Trends in the use of complementary health approaches among adults: United States, 2002-2012. *Natl Health Stat Report* 2015(79):1-16.
5. Schunck W H, Konkel A, Fischer R, Weylandt K H: Therapeutic potential of omega-3 fatty acid-derived epoxyeicosanoids in cardiovascular and inflammatory diseases. *Pharmacol Ther* 2018, 183:177-204.
6. Serhan C N, Krishnamoorthy S, Recchiuti A, Chiang N: Novel anti-inflammatory-pro-resolving mediators and their receptors. *Curr Top Med Chem* 2011, 11(6):629-647.
7. Serhan C N, Jain A, Marleau S, Clish C, Kantarci A, Behbehani B, Colgan S P, Stahl G L, Merched A, Petasis N A et al: Reduced inflammation and tissue damage in transgenic rabbits overexpressing 15-lipoxygenase and endogenous anti-inflammatory lipid mediators. *J Immunol* 2003, 171(12):6856-6865.
8. Prescott D, McKay D M: Aspirin-triggered lipoxin enhances macrophage phagocytosis of bacteria while inhibiting inflammatory cytokine production. *Am J Physiol Gastrointest Liver Physiol* 2011, 301(3):G487-497.
9. Rajasagi N K, Reddy P B, Mulik S, Gjorstrup P, Rouse B T: Neuroprotectin D1 reduces the severity of herpes simplex virus-induced corneal immunopathology. *Invest Ophthalmol Vis Sci* 2013, 54(9):6269-6279.
10. Baillie J K, Digard P: Influenza-time to target the host? *N Engl J Med* 2013, 369(2):191-193.
11. Morita M, Kuba K, Ichikawa A, Nakayama M, Katahira J, Iwamoto R, Watanabe T, Sakabe S, Daidoji T, Nakamura S et al: The lipid mediator protectin D1 inhibits influenza virus replication and improves severe influenza. *Cell* 2013, 153(1):112-125.
12. Zhu M, Wang X, Sun L, Schultzberg M, Hjorth E: Can inflammation be resolved in Alzheimer's disease? *Ther Adv Neurol Disord* 2018, 11:1756286418791107.
13. Kasikara C, Doran A C, Cai B, Tabas I: The role of non-resolving inflammation in atherosclerosis. *J Clin Invest* 2018, 128(7):2713-2723.
14. Gonzalez-Periz A, Horrillo R, Ferre N, Gronert K, Dong B, Moran-Salvador E, Titos E, Martinez-Clemente M, Lopez-Parra M, Arroyo V et al: Obesity-induced insulin resistance and hepatic steatosis are alleviated by omega-3 fatty acids: a role for resolvins and protectins. *FASEB J* 2009, 23(6):1946-1957.
15. Jin Y, Arita M, Zhang Q, Saban D R, Chauhan S K, Chiang N, Serhan C N, Dana R: Anti-angiogenesis effect of the novel anti-inflammatory and pro-resolving lipid mediators. *Invest Ophthalmol Vis Sci* 2009, 50(10):4743-4752.
16. Connor K M, SanGiovanni J P, Lofqvist C, Aderman C M, Chen J, Higuchi A, Hong S, Pravda E A, Majchrzak S, Carper D et al: Increased dietary intake of omega-3-polyunsaturated fatty acids reduces pathological retinal angiogenesis. *Nat Med* 2007, 13(7):868-873.
17. Livne-Bar I, Wei J, Liu H H, Alqawlaq S, Won G J, Tuccitto A, Gronert K, Flanagan J G, Sivak J M: Astro- 18. Arita M, Yoshida M, Hong S, Tjonahen E, Glickman J N, Petasis N A, Blumberg R S, Serhan C N: Resolvin E1, an endogenous lipid mediator derived from omega-3 eicosapentaenoic acid, protects against 2,4,6-trinitrobenzene sulfonic acid-induced colitis. *Proc Natl Acad Sci USA* 2005, 102(21):7671-7676.
19. Barnig C, Frossard N, Levy B D: Towards targeting resolution pathways of airway inflammation in asthma. *Pharmacol Ther* 2018, 186:98-113.
20. Aoki H, Hisada T, Ishizuka T, Utsugi M, Kawata T, Shimizu Y, Okajima F, Dobashi K, Mori M: Resolvin E1 dampens airway inflammation and hyperresponsiveness in a murine model of asthma. *Biochem Biophys Res Commun* 2008, 367(2):509-515.
21. Perretti M, Norling L V: Actions of SPM in regulating host responses in arthritis. *Mol Aspects Med* 2017, 58:57-64.
22. Dalli J, Zhu M, Vlasenko N A, Deng B, Haeggstrom J Z, Petasis N A, Serhan C N: The novel 13S,14S-epoxymaresin is converted by human macrophages to maresin 1 (MaR1), inhibits leukotriene A4 hydrolase (LTA4H), and shifts macrophage phenotype. *FASEB J* 2013, 27(7):2573-2583.
23. Liu Y, Fang X, Zhang X, Huang J, He J, Peng L, Ye C, Wang Y, Xue F, Ai D et al: Metabolic profiling of murine plasma reveals eicosapentaenoic acid metabolites protecting against endothelial activation and atherosclerosis. *Br J Pharmacol* 2018, 175(8):1190-1204.
24. Endo J, Sano M, Isobe Y, Fukuda K, Kang J X, Arai H, Arita M: 18-HEPE, an n-3 fatty acid metabolite released by macrophages, prevents pressure overload-induced maladaptive cardiac remodeling. *J Exp Med* 2014, 211(8):1673-1687.
25. Pochard C, Coquenlorge S, Jaulin J, Cenac N, Vergnolle N, Meurette G, Freyssinet M, Neunlist M, Rolli-Derkinderen M: Defects in 15-HETE Production and Control of Epithelial Permeability by Human Enteric Glial Cells From Patients With Crohn's Disease. *Gastroenterology* 2016, 150(1):168-180.
26. Tang Y, Zhang M J, Hellmann J, Kosuri M, Bhatnagar A, Spite M: Proresolution therapy for the treatment of delayed healing of diabetic wounds. *Diabetes* 2013, 62(2):618-627.
27. Barden A E, Mas E, Croft K D, Phillips M, Mori T A: Specialized proresolving lipid mediators in humans with the metabolic syndrome after n-3 fatty acids and aspirin. *Am J Clin Nutr* 2015, 102(6):1357-1364.
28. Miyata J, Arita M: Role of omega-3 fatty acids and their metabolites in asthma and allergic diseases. *Allergol Int* 2015, 64(1):27-34.
29. Mangino M J, Brounts L, Harms B, Heise C: Lipoxin biosynthesis in inflammatory bowel disease. *Prostaglandins Other Lipid Mediat* 2006, 79(1-2):84-92.
30. Wang C W, Colas R A, Dalli J, Arnardottir H H, Nguyen D, Hasturk H, Chiang N, Van Dyke T E, Serhan C N: Maresin 1 Biosynthesis and Proresolving Anti-infective Functions with Human-Localized Aggressive Periodontitis Leukocytes. *Infect Immun* 2015, 84(3):658-665.
31. Ringholz F C, Buchanan P J, Clarke D T, Millar R G, McDermott M, Linnane B, Harvey B J, McNally P, Urbach V: Reduced 15-lipoxygenase 2 and lipoxin A4/leukotriene B4 ratio in children with cystic fibrosis. *Eur Respir J* 2014, 44(2):394-404.
32. Werz, O, Gerstmeier J, Libreros S, De la Rosa X, Werner M, Norris, Paul C, Chiang N, Serhan C: Human macrophages differentially produce specific resolvin or leukotriene signals that depend on bacterial pathogenicity. *Nature Communications* 2018, 9(59).
33. Werner M, Jordan P M, Romp E, Czapka A, Rao Z, Kretzer C, Koeberle A, Garscha U, Pace S, Claesson H E, Serhan C N, Werz O, Gerstmeier J: Targeting biosynthetic networks of the proinflammatory and proresolving lipid metabolome. *FASEB J.* 2019 May; 33(5):6140-6153.

The invention claimed is:

1. An anti-inflammatory preparation, comprising:
   a *Boswellia* extract comprising one or more gum resins from *Boswellia* species in combination with
   a lysine, arginine, or ornithine salt of eicosapentaenoic acid (EPA) or docosahexaenoic acid (DHA), or a lysine, arginine, or ornithine salt of both EPA and DHA;
   wherein said preparation is in therapeutically effective amounts sufficient to produce greater amounts of endogenous specialized pro-resolving lipid mediators (SPMs) than either the *Boswellia* extract by itself or the lysine, arginine, or ornithine salt of EPA and DHA by itself.

2. The anti-inflammatory preparation of claim 1, wherein the SPMs are at least one selected from the group consisting of 17-HDHA, 14-HDHA, 7-HDHA, 4-HDHA, 18-HEPE, 15-HEPE, 12-HEPE, 11-HEPE, and 5-HEPE.

3. The anti-inflammatory preparation of claim 1, wherein the SPMs are at least one selected from the group consisting of RvD1, RvD2, RvD5, RvD6, MaR1, PD1, AT-PD1, PDX, RvE3, LXA4, 5,15-diHETE, LTB4, t-LTB4, 20-OH-LTB4, PGD2, PGE2, PGF2a, TXB2, 15-HETE, 12-HETE, and 11-HETE.

4. The anti-inflammatory preparation of claim 1, wherein the one or more gum resins comprise at least one selected from the group consisting of: beta-boswellic acid, acetyl-beta-boswellic acid, 11-keto-beta-boswellic acid, 3-O-acetyl-11-keto-beta-boswellic acid (AKBA), alpha-boswellic acid, 3-O-acetyl-alpha-boswellic acid, and 3-O-acetyl-beta-boswellic acid.

5. The anti-inflammatory preparation of claim 4, wherein the one or more gum resins further comprise at least one selected from the group consisting of: acid resin, gum, tetra- and pentacyclic triterpene acids, incensole acetate, phellandrene, (+)-cis- and (+)-trans-olibanic acids.

6. The anti-inflammatory preparation of claim 1, wherein the one or more gum resins comprise at least one selected from the group consisting of: *B. serrata* gum extract containing at least 10% acetyl-11-keto-beta-boswellic acid (AKBA) and at least 20% boswellic acids (BS), *B. serrata* gum resin extract containing at least 25% boswellic acids (CAS), *B. carterii* gum resin extract (AUR), and acetyl-11-keto-beta-boswellic acid (AKBA).

7. The anti-inflammatory preparation of claim 6, wherein in M1-like macrophages the amount of said preparation that contains BS is sufficient to stimulate lipid mediator biosynthesis of RvD5, PD1, PDX, MaR1, 14-HDHA, and 18-HEPE, compared to a preparation without the *Boswellia* extract.

8. The anti-inflammatory preparation of claim 6, wherein in M1-like macrophages the amount of said preparation that contains CAS is sufficient to stimulate lipid mediator biosynthesis of RvD4, RvD5, PD1, PDX, MaR1, 17-HDHA, 14-HDHA, and 18-HEPE, compared to a preparation without the *Boswellia* extract.

9. The anti-inflammatory preparation of claim 6, wherein in M1-like macrophages the amount of said preparation that contains AUR is sufficient to stimulate lipid mediator biosynthesis of PD1, PDX, MaR1, and 18-HEPE, compared to a preparation without the *Boswellia* extract.

10. The anti-inflammatory preparation of claim 6, wherein in M1-like macrophages the amount of said preparation that contains AKBA is sufficient to stimulate lipid mediator biosynthesis of RvD5, PD1, PDX, MaR1, 17-HDHA, 14-HDHA, and 18-HEPE, compared to a preparation without the *Boswellia* extract.

11. The anti-inflammatory preparation of claim 6, wherein in M2-like macrophages the amount of said preparation that contains BS is sufficient to stimulate lipid mediator biosynthesis of RvD5, PD1, PDX, MaR1, 17-HDHA, 14-HDHA, and 18-HEPE, compared to a preparation without the *Boswellia* extract.

12. The anti-inflammatory preparation of claim 6, wherein in M2-like macrophages the amount of said preparation that contains CAS is sufficient to stimulate lipid mediator biosynthesis of RvD5, PD1, PDX, MaR1, 17-HDHA, 14-HDHA, and 18-HEPE, compared to a preparation without the *Boswellia* extract.

13. The anti-inflammatory preparation of claim 6, wherein in M2-like macrophages the amount of said preparation that contains AUR is sufficient to stimulate lipid mediator biosynthesis of RvD5, PDX, MaR1, 17-HDHA, 14-HDHA, and 18-HEPE, compared to a preparation without the *Boswellia* extract.

14. The anti-inflammatory preparation of claim 6, wherein in M2-like macrophages the amount of said preparation that contains AKBA is sufficient to stimulate lipid mediator biosynthesis of RvD5, MaR1, 17-HDHA, 14-HDHA, and 18-HEPE, compared to a preparation without the *Boswellia* extract.

15. The anti-inflammatory preparation of claim 1 that comprises at least 10 weight % of the *Boswellia* extract and/or at least 10 weight-% of the salt of eicosapentaenoic acid (EPA) and/or docosahexaenoic acid (DHA).

16. The anti-inflammatory preparation of claim 1 that further comprises at least one phospholipid selected from a deoiled phospholipid with a phosphatidylcholine content of greater than 70 weight % and a phosphatidylethanolamine content lower than 5 weight %; or a non-hydrogenated phospholipid having an oleic and/or linoleic acid content of greater than 70 weight % of total fatty acids.

17. The anti-inflammatory preparation of claim 1, wherein a mass ratio of phospholipid to fatty acid salt is greater than 0.01; and/or a weight ratio of *Boswellia* extract with relation to the salt of eicosapentaenoic acid (EPA) and/or docosahexaenoic acid (DHA) is between 0.5:1 to 1:0.5.

18. The anti-inflammatory preparation of claim 1 in the form of a targeted release formulation.

19. The anti-inflammatory preparation of claim 1, further comprising one or more anthocyanins, vitamins, minerals, fiber, fatty acids, amino acids, or proteins; or in the form of a food supplement or pharmaceutical product.

20. The anti-inflammatory preparation of claim 1 in the form of a tablet, pellet, microparticle or microparticulate composition, or capsule or in a form formulated for topical application.

21. The anti-inflammatory preparation of claim 1 is in a form suitable for treating or preventing one or more chronic inflammatory diseases.

22. The anti-inflammatory preparation of claim 1, wherein the extract is prepared from *Boswellia serrata, Boswellia carterii, Boswellia papyrifera, Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and/or *Boswellia socotrana*.

23. The anti-inflammatory preparation of claim 1, wherein the extract is prepared by using hydro-distillation, steam distillation, extraction by percolation, extraction under ultrasonic waves, solvent extraction, Soxhlet's extraction, supercritical fluid extraction or membrane nanofiltration.

\* \* \* \* \*